United States Patent
Gylland et al.

(10) Patent No.: US 11,246,985 B2
(45) Date of Patent: Feb. 15, 2022

(54) INFUSION PUMP SYSTEM AND METHOD WITH COMMON LINE AUTO FLUSH

(71) Applicant: ICU Medical, Inc., San Clemente, CA (US)

(72) Inventors: Jeffrey James Gylland, Cedarburg, WI (US); Gerald William Brann, Antiosh, IL (US); James Duane Jacobson, Lindenhurst, IL (US); Arthur E. Webb, Escondido, CA (US); James Cudney, Santee, CA (US); Nursel Asikhan-Berlinguette, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 457 days.

(21) Appl. No.: 16/301,379

(22) PCT Filed: May 10, 2017

(86) PCT No.: PCT/US2017/032017
§ 371 (c)(1),
(2) Date: Nov. 13, 2018

(87) PCT Pub. No.: WO2017/197024
PCT Pub. Date: Nov. 16, 2017

(65) Prior Publication Data
US 2020/0324044 A1 Oct. 15, 2020

Related U.S. Application Data

(60) Provisional application No. 62/336,191, filed on May 13, 2016.

(51) Int. Cl.
*A61M 5/14* (2006.01)
*G16H 20/17* (2018.01)
(Continued)

(52) U.S. Cl.
CPC .............. *A61M 5/172* (2013.01); *A61M 5/14* (2013.01); *A61M 5/142* (2013.01); *A61M 5/145* (2013.01);
(Continued)

(58) Field of Classification Search
CPC .... A61M 5/172; A61M 5/14; A61M 5/14248; A61M 5/16881; A61M 5/16831;
(Continued)

(56) References Cited

U.S. PATENT DOCUMENTS

| | | | |
|---|---|---|---|
| 3,401,337 A | 9/1968 | Beusman et al. | |
| 3,484,681 A | 12/1969 | Grady, Jr. et al. | |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

WO2015/134478, Ledford, et al, Infusion Pump Drug Delivery Profiles, Systems, and Methods. (Year: 2015).*

(Continued)

*Primary Examiner* — Manuel A Mendez
(74) *Attorney, Agent, or Firm* — Knobbe Martens Olson & Bear, LLP

(57) ABSTRACT

An infusion pump system and method with common line auto flush, wherein the infusion pump system has a first reservoir, a second reservoir, a junction, a common line having one end in fluid connection with the junction and having a terminal fluid delivery end, and an infusion pump. The method includes infusing the first fluid at a first rate along a first flow path; entering a common line flush volume value for the common line; switching from the first flow path to a second flow path; driving the second fluid at the first rate (Continued)

along the second flow path; monitoring volume of the second fluid driven at the first rate; and driving the second fluid at a second rate along the second flow path when the monitored volume is equal to or greater than the common line flush volume value.

19 Claims, 16 Drawing Sheets

(51) Int. Cl.
*A61M 5/172* (2006.01)
*A61M 5/145* (2006.01)
*A61M 5/168* (2006.01)
*A61M 5/142* (2006.01)
*G16H 40/67* (2018.01)
*G16H 50/20* (2018.01)
*G05B 19/042* (2006.01)
*G05D 7/06* (2006.01)
*G06F 3/0481* (2022.01)

(52) U.S. Cl.
CPC .......... *A61M 5/1407* (2013.01); *A61M 5/168* (2013.01); *A61M 5/16827* (2013.01); *A61M 5/16831* (2013.01); *G05B 19/042* (2013.01); *G05D 7/0635* (2013.01); *G16H 20/17* (2018.01); *G16H 40/67* (2018.01); *G16H 50/20* (2018.01); *A61M 2005/1403* (2013.01); *A61M 2205/3331* (2013.01); *A61M 2205/3334* (2013.01); *A61M 2205/3379* (2013.01); *A61M 2205/50* (2013.01); *A61M 2205/502* (2013.01); *A61M 2205/52* (2013.01); *G05B 2219/25312* (2013.01); *G06F 3/0481* (2013.01)

(58) Field of Classification Search
CPC .......... A61M 5/14276; A61M 5/16854; G16H 20/17; G16H 70/40; G16H 40/67; G16H 60/20
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |

(56) References Cited

U.S. PATENT DOCUMENTS

| | | |
|---|---|---|
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalaute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Bloomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |

(56) References Cited

U.S. PATENT DOCUMENTS

| | | |
|---|---|---|
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A * | 4/1994 | Epstein ............ A61M 5/14224 128/DIG. 13 |
| 5,304,216 A * | 4/1994 | Wallace ............... A61F 7/0241 607/108 |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |

(56) References Cited

U.S. PATENT DOCUMENTS

| | | |
|---|---|---|
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |

(56) References Cited

U.S. PATENT DOCUMENTS

| | | |
|---|---|---|
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |

(56) References Cited

U.S. PATENT DOCUMENTS

| | | |
|---|---|---|
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouola et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |

(56) References Cited

U.S. PATENT DOCUMENTS

| | | |
|---|---|---|
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenkow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,981,073 B2 | 7/2011 | Mollstam |
| 7,981,082 B2 | 7/2011 | Wang et al. |
| 8,002,736 B2 * | 8/2011 | Patrick .............. A61M 5/16827 604/83 |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blornquist |
| 8,175,668 B1 | 5/2012 | Nabutovsky et al. |
| 8,177,739 B2 | 5/2012 | Cartledge et al. |
| 8,185,322 B2 | 5/2012 | Schroeder et al. |
| 8,219,413 B2 | 7/2012 | Martinez et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,449,524 B2 | 5/2013 | Braig et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |

(56) References Cited

U.S. PATENT DOCUMENTS

| | | | |
|---|---|---|---|
| 9,138,526 B2 | 9/2015 | Ware et al. | |
| 9,190,010 B2 | 11/2015 | Vik et al. | |
| 9,240,002 B2 | 1/2016 | Hume et al. | |
| 9,272,089 B2 | 3/2016 | Jacobson et al. | |
| 9,333,291 B2 | 5/2016 | Jacobson et al. | |
| 9,381,296 B2 | 7/2016 | Arrizza et al. | |
| 9,393,362 B2 | 7/2016 | Cozmi et al. | |
| 9,468,718 B2 | 10/2016 | Hung et al. | |
| 9,498,583 B2 | 11/2016 | Sur et al. | |
| 9,707,341 B2 | 7/2017 | Dumas, III et al. | |
| 9,764,087 B2* | 9/2017 | Peterfreund | A61M 5/16827 |
| 9,852,265 B1 | 12/2017 | Treacy et al. | |
| 9,943,269 B2 | 4/2018 | Muhsin et al. | |
| 9,995,611 B2 | 6/2018 | Ruchti et al. | |
| 10,022,498 B2 | 7/2018 | Ruchti et al. | |
| 10,046,112 B2 | 8/2018 | Oruklu et al. | |
| 10,089,055 B1 | 10/2018 | Fryman | |
| 10,166,328 B2 | 1/2019 | Oruklu et al. | |
| 10,342,917 B2 | 7/2019 | Shubinsky et al. | |
| 2001/0007636 A1 | 7/2001 | Butterfield | |
| 2001/0014769 A1 | 8/2001 | Bufe et al. | |
| 2001/0015099 A1 | 8/2001 | Blaine | |
| 2001/0016056 A1 | 8/2001 | Westphal et al. | |
| 2001/0032099 A1 | 10/2001 | Joao | |
| 2001/0037060 A1 | 11/2001 | Thompson et al. | |
| 2001/0041869 A1 | 11/2001 | Causey et al. | |
| 2001/0044731 A1 | 11/2001 | Coffman et al. | |
| 2002/0003892 A1 | 1/2002 | Iwanaga | |
| 2002/0007116 A1 | 1/2002 | Zatezalo et al. | |
| 2002/0013545 A1 | 1/2002 | Soltanpour et al. | |
| 2002/0013551 A1 | 1/2002 | Zaitsu et al. | |
| 2002/0015018 A1 | 2/2002 | Shimazu et al. | |
| 2002/0018720 A1 | 2/2002 | Carlisle et al. | |
| 2002/0029776 A1 | 3/2002 | Blomquist | |
| 2002/0031838 A1 | 3/2002 | Meinhart et al. | |
| 2002/0032583 A1 | 3/2002 | Joao | |
| 2002/0040208 A1 | 4/2002 | Flaherty et al. | |
| 2002/0044059 A1 | 4/2002 | Reeder et al. | |
| 2002/0045806 A1 | 4/2002 | Baker, Jr. et al. | |
| 2002/0082728 A1 | 6/2002 | Mueller et al. | |
| 2002/0083771 A1 | 7/2002 | Khuri-Yakub et al. | |
| 2002/0085952 A1 | 7/2002 | Ellingboe et al. | |
| 2002/0087115 A1 | 7/2002 | Hartlaub | |
| 2002/0095486 A1 | 7/2002 | Bahl | |
| 2002/0099282 A1 | 7/2002 | Knobbe et al. | |
| 2002/0099334 A1 | 7/2002 | Hanson et al. | |
| 2002/0143580 A1 | 10/2002 | Bristol et al. | |
| 2002/0147389 A1 | 10/2002 | Cavallaro et al. | |
| 2002/0152239 A1 | 10/2002 | Bautista-Lloyd et al. | |
| 2002/0168278 A1 | 11/2002 | Jeon et al. | |
| 2002/0173703 A1 | 11/2002 | Lebel et al. | |
| 2002/0183693 A1 | 12/2002 | Peterson et al. | |
| 2003/0009244 A1 | 1/2003 | Engleson | |
| 2003/0013959 A1 | 1/2003 | Grunwald et al. | |
| 2003/0018308 A1 | 1/2003 | Tsai | |
| 2003/0025602 A1 | 2/2003 | Medema et al. | |
| 2003/0028082 A1 | 2/2003 | Thompson | |
| 2003/0030001 A1 | 2/2003 | Cooper et al. | |
| 2003/0045840 A1 | 3/2003 | Burko | |
| 2003/0050621 A1 | 3/2003 | Lebel et al. | |
| 2003/0060688 A1 | 3/2003 | Ciarniello et al. | |
| 2003/0060765 A1 | 3/2003 | Campbell et al. | |
| 2003/0065537 A1 | 4/2003 | Evans | |
| 2003/0065589 A1 | 4/2003 | Giacchetti | |
| 2003/0073954 A1 | 4/2003 | Moberg et al. | |
| 2003/0079746 A1 | 5/2003 | Hickle | |
| 2003/0083583 A1 | 5/2003 | Kovtun et al. | |
| 2003/0091442 A1 | 5/2003 | Bush et al. | |
| 2003/0104982 A1 | 6/2003 | Wittmann et al. | |
| 2003/0106553 A1 | 6/2003 | Vanderveen | |
| 2003/0125662 A1 | 7/2003 | Bui | |
| 2003/0130616 A1 | 7/2003 | Steil | |
| 2003/0135087 A1 | 7/2003 | Hickle et al. | |
| 2003/0136193 A1 | 7/2003 | Fujimoto | |
| 2003/0139701 A1 | 7/2003 | White et al. | |
| 2003/0140928 A1 | 7/2003 | Bui et al. | |
| 2003/0141981 A1 | 7/2003 | Bui et al. | |
| 2003/0143746 A1 | 7/2003 | Sage, Jr. | |
| 2003/0144878 A1 | 7/2003 | Wilkes et al. | |
| 2003/0158508 A1 | 8/2003 | DiGianfilippo | |
| 2003/0160683 A1 | 8/2003 | Blomquist | |
| 2003/0163789 A1 | 8/2003 | Blomquist | |
| 2003/0173408 A1 | 9/2003 | Mosher, Jr. et al. | |
| 2003/0186833 A1* | 10/2003 | Huff | C08F 283/06 |
| | | | 510/475 |
| 2003/0187338 A1 | 10/2003 | Say et al. | |
| 2003/0200116 A1 | 10/2003 | Forrester | |
| 2003/0204274 A1 | 10/2003 | Ullestad et al. | |
| 2003/0204416 A1 | 10/2003 | Acharya | |
| 2003/0212364 A1 | 11/2003 | Mann et al. | |
| 2003/0212379 A1 | 11/2003 | Bylund et al. | |
| 2003/0216682 A1* | 11/2003 | Junker | G16H 20/17 |
| | | | 604/65 |
| 2003/0217962 A1 | 11/2003 | Childers et al. | |
| 2003/0233071 A1 | 12/2003 | Gillespie, Jr. et al. | |
| 2004/0030277 A1 | 2/2004 | O'Mahony et al. | |
| 2004/0047736 A1 | 3/2004 | Nose et al. | |
| 2004/0057226 A1 | 3/2004 | Berthou et al. | |
| 2004/0064342 A1 | 4/2004 | Browne et al. | |
| 2004/0073125 A1 | 4/2004 | Lovett et al. | |
| 2004/0073161 A1 | 4/2004 | Tachibana | |
| 2004/0077996 A1 | 4/2004 | Jasperson et al. | |
| 2004/0082908 A1 | 4/2004 | Whitehurst | |
| 2004/0082918 A1 | 4/2004 | Evans et al. | |
| 2004/0104271 A1 | 6/2004 | Martucci et al. | |
| 2004/0119753 A1 | 6/2004 | Zencke | |
| 2004/0120825 A1 | 6/2004 | Bouton et al. | |
| 2004/0145114 A1 | 6/2004 | Ippolito et al. | |
| 2004/0128162 A1 | 7/2004 | Schlotterbeck et al. | |
| 2004/0133166 A1 | 7/2004 | Moberg et al. | |
| 2004/0147034 A1 | 7/2004 | Gore et al. | |
| 2004/0149823 A1 | 8/2004 | Aptekar | |
| 2004/0152970 A1 | 8/2004 | Hunter et al. | |
| 2004/0158193 A1 | 8/2004 | Bui et al. | |
| 2004/0167464 A1 | 8/2004 | Ireland et al. | |
| 2004/0167465 A1 | 8/2004 | Kohler | |
| 2004/0167804 A1 | 8/2004 | Simpson | |
| 2004/0172222 A1 | 9/2004 | Simpson et al. | |
| 2004/0172283 A1 | 9/2004 | Vanderveen | |
| 2004/0172289 A1 | 9/2004 | Kozic et al. | |
| 2004/0172302 A1 | 9/2004 | Martucci et al. | |
| 2004/0176984 A1 | 9/2004 | White et al. | |
| 2004/0181314 A1 | 9/2004 | Zaleski | |
| 2004/0193025 A1 | 9/2004 | Steil et al. | |
| 2004/0193325 A1 | 9/2004 | Bonderud | |
| 2004/0193328 A1 | 9/2004 | Butterfield et al. | |
| 2004/0193453 A1 | 9/2004 | Butterfield et al. | |
| 2004/0204638 A1 | 10/2004 | Diab et al. | |
| 2004/0204673 A1 | 10/2004 | Flaherty et al. | |
| 2004/0220517 A1 | 11/2004 | Starkweather et al. | |
| 2004/0225252 A1 | 11/2004 | Gillespie et al. | |
| 2004/0225409 A1 | 11/2004 | Duncan et al. | |
| 2004/0232219 A1 | 11/2004 | Fowler | |
| 2004/0253123 A1 | 12/2004 | Xie et al. | |
| 2004/0254434 A1 | 12/2004 | Goodnow et al. | |
| 2004/0254513 A1 | 12/2004 | Shang et al. | |
| 2005/0021006 A1 | 1/2005 | Tonnies | |
| 2005/0021297 A1 | 1/2005 | Hartlaub | |
| 2005/0022274 A1 | 1/2005 | Campbell et al. | |
| 2005/0038680 A1 | 2/2005 | McMahon | |
| 2005/0055242 A1 | 3/2005 | Bello et al. | |
| 2005/0055244 A1 | 3/2005 | Mullan et al. | |
| 2005/0065465 A1 | 3/2005 | Lebel et al. | |
| 2005/0075544 A1 | 4/2005 | Shapiro et al. | |
| 2005/0096593 A1 | 5/2005 | Pope et al. | |
| 2005/0099624 A1 | 5/2005 | Staehr | |
| 2005/0107923 A1 | 5/2005 | Vanderveen | |
| 2005/0119914 A1 | 6/2005 | Batch | |
| 2005/0131739 A1 | 6/2005 | Rabinowitz et al. | |
| 2005/0137522 A1 | 6/2005 | Aoki | |
| 2005/0143864 A1 | 6/2005 | Blomquist | |
| 2005/0145010 A1 | 7/2005 | Vanderveen et al. | |
| 2005/0171503 A1 | 8/2005 | Van Den Berghe et al. | |
| 2005/0171815 A1 | 8/2005 | Vanderveen | |

(56) References Cited

U.S. PATENT DOCUMENTS

| | | |
|---|---|---|
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 * | 9/2005 | Shelton .................. G16H 20/17 604/890.1 |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 * | 3/2006 | Bollish ............... A61M 1/3451 604/31 |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0172030 A1 | 7/2008 | Blomquist et al. |
| 2008/0177254 A1 * | 7/2008 | Shelton .................. G16H 20/17 604/891.1 |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |

(56) References Cited

U.S. PATENT DOCUMENTS

| | | |
|---|---|---|
| 2009/0097029 A1 | 4/2009 | Tokhtuev et al. |
| 2009/0112155 A1 | 4/2009 | Zhao |
| 2009/0124963 A1 | 5/2009 | Hogard et al. |
| 2009/0124964 A1 | 5/2009 | Leach et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2009/0281460 A1* | 11/2009 | Lowery ............ A61B 5/150389 600/584 |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1* | 5/2010 | Jacobson .......... A61M 5/16886 604/151 |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0317093 A1 | 12/2010 | Turewicz et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0137241 A1 | 6/2011 | DelCastilio et al. |
| 2011/0144595 A1 | 6/2011 | Cheng |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0320049 A1 | 12/2011 | Chossat et al. |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0041342 A1 | 2/2013 | Bernini et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0197930 A1 | 8/2013 | Garibaldi et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0274576 A1* | 10/2013 | Amirouche ........ A61B 5/14503 600/365 |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0224829 A1 | 8/2014 | Capone et al. |
| 2014/0267563 A1 | 9/2014 | Baca et al. |
| 2014/0303591 A1* | 10/2014 | Peterfreund .......... A61M 5/142 604/500 |
| 2015/0025453 A1* | 1/2015 | Ledford ............. A61M 5/142 604/67 |
| 2015/0033073 A1 | 1/2015 | Yang et al. |
| 2015/0168958 A1 | 6/2015 | Downie et al. |
| 2015/0343141 A1 | 12/2015 | Lindo et al. |
| 2016/0042264 A1 | 2/2016 | Borges et al. |
| 2016/0103960 A1 | 4/2016 | Hume et al. |
| 2016/0110088 A1 | 4/2016 | Vik et al. |
| 2016/0151560 A1 | 6/2016 | Toro et al. |
| 2016/0151562 A1 | 6/2016 | Magers et al. |
| 2016/0175517 A1 | 6/2016 | Sileika et al. |
| 2016/0193604 A1 | 7/2016 | McFarland et al. |
| 2016/0256622 A1 | 9/2016 | Day et al. |
| 2016/0339167 A1* | 11/2016 | Ledford ................ G16H 20/17 |
| 2017/0043089 A1 | 2/2017 | Handler |

(56) References Cited

U.S. PATENT DOCUMENTS

| | | |
|---|---|---|
| 2018/0018440 A1 | 1/2018 | Sugawara |
| 2018/0028749 A1 | 2/2018 | Dumas, III et al. |
| 2019/0091401 A1 | 3/2019 | Ruchti et al. |
| 2019/0101425 A1 | 4/2019 | Ruchti et al. |
| 2019/0117890 A1 | 4/2019 | Oruklu et al. |
| 2019/0196770 A1 | 6/2019 | Fryman |

FOREIGN PATENT DOCUMENTS

| | | |
|---|---|---|
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-520270 | 7/2007 |
| JP | 2008-249400 | 10/2008 |
| JP | 4322661 | 6/2009 |
| JP | 2010-063767 | 3/2010 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2010/017279 | 2/2010 |
| WO | WO 2010/075371 | 7/2010 |

(56) References Cited

FOREIGN PATENT DOCUMENTS

| WO | WO 2010/099313 | | 9/2010 |
|---|---|---|---|
| WO | WO 2010/114929 | | 10/2010 |
| WO | WO 2010/119409 | | 10/2010 |
| WO | WO 2010/124127 | | 10/2010 |
| WO | WO 2010/135646 | | 11/2010 |
| WO | WO 2010/135654 | | 11/2010 |
| WO | WO 2010/135670 | | 11/2010 |
| WO | WO 2010/135686 | | 11/2010 |
| WO | WO 2010/148205 | | 12/2010 |
| WO | WO 2011/017778 | | 2/2011 |
| WO | WO 2011/080188 | | 7/2011 |
| WO | WO 2011/109774 | | 9/2011 |
| WO | WO 2012/042763 | | 4/2012 |
| WO | WO 2012/082599 | | 6/2012 |
| WO | WO 2012/167090 | | 12/2012 |
| WO | WO 2013/096769 | | 6/2013 |
| WO | WO 2015/134478 | A1 | 9/2015 |
| WO | WO 2017/051271 | | 3/2017 |
| WO | WO 2017/197024 | | 11/2017 |
| WO | WO 2017/214441 | | 12/2017 |

OTHER PUBLICATIONS

International Search Report for International App. No. PCT/US2017/032017, dated Jul. 20, 2017, in 1 page.
Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
ALARIS® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
International Preliminary Report on Patentability and Written Opinion received in PCT Application No. PCT/US2017/032017, dated Nov. 22, 2018 in 11 pages.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.

(56) References Cited

OTHER PUBLICATIONS

Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.

Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.

Magaji et al., "Inpatient Management of Hyperglycemia and Diabetes", Clinical Diabetes, 2011, vol. 29, No. 1, pp. 3-9.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.

Merry et al., "A New, Safety-Oriented, Integrated Drug Administration and Automated Anesthesia Record System", Anesthesia & Analgesia, Aug. 2001, vol. 93, No. 2 pp. 385-390.

Microchip Technology Inc., "MTA11200B; TrueGauge™ Intelligent Battery Management I.C.", https://www.elektronik.robla.eu/pdf/stock/mcp/mta11200b.pdf, 1995, pp. 44.

Moghissi, Etie, MD, FACP, FACE, "Hyperglycemia in Hospitalized Patients", A Supplement to ACP Hospitalist, Jun. 15, 2008, pp. 32.

Nuckols et al., "Programmable Infusion Pumps in ICUs: An Analysis of Corresponding Adverse Drug Events", Journal of General Internal Medicine, 2007, vol. 23, Supp. 1, pp. 41-45.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

SGS—Thomson Microelectronics, "L6219—Stepper Motor Drive", Datasheet, Dec. 1996, pp. 10.

SGS—Thomson Microelectronics, "PBL3717A—Stepper Motor Drive", Datasheet, Apr. 1993, pp. 11.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Smith, Joe, "Infusion Pump Informatics", CatalyzeCare: Transforming Healthcare, as printed May 12, 2011, pp. 2.

Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

\* cited by examiner

| S33 | | |
|---|---|---|
| A | Oncology (1 of 3) | |
| | Change CCA | |
| No Drug Selected | | |
| DOPamine | 40mg/500mL | |
| Felicium | 25mg/750mL | |
| Metazine | 25mg/20mL | |
| locaine | 30mg/30mL | |
| NIVOlumab | 100mg/510mL | |
| Normal Sanine | 100mL | |
| Select then press to Choose | | |
| Press 0-9 to Sort this list | | |
| Page Up | Page Down | Choose | Previous Screen |

FIG. 4B

| S22 | | B |
|---|---|---|
| A | | |
| | 0 Rate mL/hr | 0 |
| | 0 Vol Inf mL | 0 |
| Callback | Oncology | Piggyback |
| Press A to Cancel Standby | | |
| Select STOP key to Clear? | | |
| Standby | A | B | Settings/Vols/CCA |

| S30 | Program | B |
|---|---|---|
| | NIVOlumab | |

| | |
|---|---|
| Conc | 100 mg 510 mL |
| Weight | 50 kg |
| Dose | 0 mcg/kg/min |
| Rate | 0 mL/hr |
| VTBI | 0 mL |
| Duration | 00:00 hh:min |
| Callback | Oncology   Piggyback |

START confirmation
Flush Line: To flush line when Complete

| Delay | | Return to A/B |
|---|---|---|

FIG. 4H

| S39 | Oncology (1 of 3) | B |
|---|---|---|
| | Change CCA | |

No Drug Selected

| | |
|---|---|
| Ephemerol | 1mg/10mL |
| DOPamine | 40mg/500mL |
| Felicium | 25mg/750mL |
| Metazine | 25mg/20mL |
| locaine | 30mg/30mL |
| NIVOlumab | 100mg/510mL |

Select then press to Choose
Press 0-9 to Sort this list

| Page Up | Page Down | Choose | Previous Screen |
|---|---|---|---|

| Program | B |
|---|---|

NIVOlumab
Conc 100 mg 510 mL
Weight 50 kg

Dose 100 mcg/kg/min
Rate 375 mL/hr
VTBI 500 mL
Duration 01:20 hh:min

Callback [Oncology] Piggyback

START confirmation
Flush Line: To flush line when Complete

| Delay | Auto Flush | Return to A/B |
|---|---|---|

| A | Flush Volume |
|---|---|

Normal Saline

Rate 375 mL/hr
Flush Volume 0 mL
Duration 00:00 hh:min
Maximum Flush Volume 30 mL Enter Value

| | | Cancel |
|---|---|---|

| S146 | A | Flush Volume | |
|---|---|---|---|
| | | Normal Saline | |
| | Rate | | 375 mL/hr |
| | Flush Volume | | 20 mL |
| | Duration | | 00:00 hh:min |
| | Maximum Flush Volume | | 30 mL |
| Enter Value | | | Cancel |

| S43 | A | Confirm Program | B |
|---|---|---|---|
| | Normal Saline<br>Flush Solution | | NIVOlumab<br>400mg 500mL |
| | Weight | 50 kg | |
| | Dose | | 100 mcg/kg/min |
| | Rate | | 375 mL/hr |
| | VTBI | | 500 mL (20 mL Flush) |
| | Duration | | 01:20 hh:min |
| | Callback | Oncology | No  Edit  Piggyback |
| Yes Start delivery | | | No |
| Yes | | Standby | |

| S22 | A | PENDING | PUMPING | B |
|---|---|---|---|---|
| | Normal Saline | | NIVOlumab 100mg 510mL | |

Dose  100 mcg/kg/min
125      375
Rate mL/hr
3
Vol Inf  0
mL  [Oncology]

Callback     Piggyback

Select STOP key to Clear?

| Standby | A | B | Settings/Vols/CCA |

| S22 | A | FLUSH | STOPPED | B |
|---|---|---|---|---|
| | Normal Saline | | NIVOlumab 400mg 500mL | |

Dose  100 mcg/kg/min
375      0
Rate mL/hr
3
Vol Inf  500
mL

Callback     Piggyback

Select STOP key to Clear?

| Standby | A | B | Settings/Vols/CCA |

440

FIG. 4N

INFUSION PUMP SYSTEM AND METHOD WITH COMMON LINE AUTO FLUSH

BACKGROUND OF THE INVENTION

Field of the Invention

The present invention relates to medical devices. More specifically, the invention relates to infusion pump systems.

Infusion pumps are medical devices that deliver fluids, including nutrients and medications such as antibiotics, chemotherapy drugs, and pain relievers, in controlled amounts. Many types of pumps, including large volume, patient-controlled analgesia (PCA), elastomeric, syringe, enteral, and insulin pumps, are used worldwide in healthcare facilities, such as hospitals, and in the home. Clinicians and patients rely on pumps for safe and accurate administration of fluids and medications.

It is desirable to provide more than one therapeutic fluid from the infusion pump for some treatment regimens. Presently, two fluid reservoirs with different therapeutic fluids are connected to the infusion pump and then delivered through a common line having a terminal fluid delivery end. The first therapeutic fluid and second therapeutic fluid are administered alternately by switching the fluid flow path between the first reservoir and the second reservoir.

Unfortunately, the therapeutic fluid remaining in the common line creates problems when switching between the two therapeutic fluids. First, the remaining therapeutic fluid must be cleared from the common line before the next therapeutic fluid begins administration, delaying the next therapeutic fluid from reaching the patient. Second, when the therapeutic fluids are administered at different rates, the therapeutic fluid remaining in the common line will be administered at the rate of the new fluid being administered, e.g., the remaining first therapeutic fluid will be administered at the rate specified for the second therapeutic fluid. This can result in the patient from receiving more or less than the optimum therapy with respect to the first therapeutic fluid. Third, the remaining therapeutic fluid may not be correctly accounted for, potentially creating errors in the values indicated at the infusion pump. While the pump data will be correct in terms of infusion rates over given times, the actual fluid delivery to the terminal fluid delivery end at the patient is not correctly captured in pump and system data.

It would be desirable to have infusion pump systems and methods with common line auto flush that would overcome the above disadvantages.

SUMMARY OF THE DISCLOSURE

One aspect of the present invention provides a method to infuse fluids with an infusion pump system, the infusion pump system having a first reservoir containing a first fluid, a second reservoir containing a second fluid, a junction in fluid communication with the first reservoir and the second reservoir, a common line in fluid communication with the junction at one end and having a terminal fluid delivery end, and an infusion pump operable to drive fluid through the common line. The method includes infusing the first fluid at a first rate along a first flow path including the first reservoir, the junction, and the common line; entering a common line flush volume value for the common line; switching from the first flow path to a second flow path including the second reservoir, the junction, and the common line; driving the second fluid at the first rate along the second flow path; monitoring volume of the second fluid driven at the first rate; and driving the second fluid at a second rate along the second flow path when the monitored volume is equal to or greater than the common line flush volume value.

Another aspect of the present invention provides an infusion pump system including a first reservoir containing a first fluid; a second reservoir containing a second fluid; a junction in fluid communication with the first reservoir and the second reservoir; a common line in fluid communication with the junction at one end and a terminal fluid delivery end; and an infusion pump operable to drive fluid through the common line. The infusion pump is operable to infuse the first fluid at a first rate along a first flow path including the first reservoir, the junction, and the common line; receive a common line flush volume value for the common line; switch from the first flow path to a second flow path including the second reservoir, the junction, and the common line; drive the second fluid at the first rate along the second flow path; monitor volume of the second fluid driven at the first rate; and drive the second fluid at a second rate along the second flow path when the monitored volume is equal to or greater than the common line flush volume value.

Yet another aspect of the present invention provides an infusion pump, the infusion pump being operably connected to a common line in fluid communication with a junction at one end and having a terminal fluid delivery end, the junction being in fluid communication with a first reservoir containing a first fluid and a second reservoir containing a second fluid. The infusion pump includes a memory operable to store programming code; a flow controller operably connected to the memory; and a fluid driver operably connected to receive a control signal from the flow controller, the fluid driver being operable to drive fluid through the common line. The flow controller is operable to execute the programming code and provide the control signal to the fluid driver in response to the programming code. The fluid driver is responsive to the control signal to infuse the first fluid at a first rate along a first flow path including the first reservoir, the junction, and the common line; receive a common line flush volume value for the common line; switch from the first flow path to a second flow path including the second reservoir, the junction, and the common line; drive the second fluid at the first rate along the second flow path; monitor volume of the second fluid driven at the first rate; and drive the second fluid at a second rate along the second flow path when the monitored volume is equal to or greater than the common line flush volume value.

The foregoing and other features and advantages of the invention will become further apparent from the following detailed description of the presently preferred embodiments, read in conjunction with the accompanying drawings. The detailed description and drawings are merely illustrative of the invention rather than limiting. The scope of the invention is defined by the appended claims and equivalents thereof.

In certain embodiments, a control system can control operation of an infusion pump system. The infusion pump system can include a first reservoir that can hold a first fluid, a second reservoir configured to hold a second fluid, a junction in fluid communication with the first reservoir and the second reservoir, a common line in fluid communication with the junction and having a terminal fluid delivery end, and an infusion pump operable to drive fluid through the common line toward the terminal fluid delivery end. The control system can include one or more hardware processors for executing instructions. The control system can receive instructions for delivery of a first fluid at a first rate followed by a second fluid at a second rate. The control system can further infuse a first fluid at a first rate along a first flow path.

The control system can also determine a first volume to clear the first fluid from a common line. The control system can infuse a second fluid at the first rate along a second flow path. The control system can monitor a second volume of the second fluid infused at the first rate. The control system can determine when the monitored volume of the second fluid meets or exceeds the first volume. The control system can change infusion of the second fluid to a second rate along the second flow path based on the determination when the monitored volume of the second fluid meets or exceeds the first volume.

The control system of the preceding paragraph can have any sub-combination of the following features: wherein the first volume is received from a user input; wherein the first volume is stored in a memory; wherein the first volume is retrieved over a network; wherein the first volume is predetermined; wherein the first volume is based on the first fluid; wherein the first rate is different than the second rate; wherein the instructions for the delivery are received from an input via a user interface; wherein the one or more hardware processors can automatically generate a user interface configured to receive an input for the first volume based on a determination of sequential delivery of two different fluids; wherein the one or more hardware processors can control a valve, wherein the valve is configured to switch the infusion of the first fluid along the first flow path to the infusion of the second fluid along the second path; wherein the one or more hardware processors are configured to transmit a control signal to begin the infusion; wherein the one or more hardware processors are configured to transmit a control signal to stop the infusion.

A method for controlling operation of an infusion pump system, the infusion pump system comprising a first reservoir configured to hold a first fluid, a second reservoir configured to hold a second fluid, a junction in fluid communication with the first reservoir and the second reservoir, a common line in fluid communication with the junction and having a terminal fluid delivery end, and an infusion pump operable to drive fluid through the common line toward the terminal fluid delivery end. The method can include receiving instructions for delivery of a first fluid at a first rate followed by a second fluid at a second rate. The method can also include infusing a first fluid at a first rate along a first flow path. The method can further include determining a first volume to clear the first fluid from a common line. In some embodiments, the method includes infusing a second fluid at the first rate along a second flow path. The method can include monitoring a second volume of the second fluid infused at the first rate. The method can also include determining when the monitored volume of the second fluid meets or exceeds the first volume. The method also includes changing infusion of the second fluid to a second rate along the second flow path based on the determination when the monitored volume of the second fluid meets or exceeds the first volume.

The method of preceding paragraph can have any sub-combination of the following features: wherein the first volume is received from a user input; wherein the first volume is stored in a memory; wherein the first volume is retrieved over a network; wherein the first volume is predetermined; wherein the first volume is based on the first fluid; wherein the first rate is different than the second rate; wherein the instructions for the delivery are received from an input via a user interface; further comprising automatically generating a user interface configured to receive an input for the first volume based on a determination of sequential delivery of two different fluids; further comprising controlling a valve, wherein the valve is configured to switch the infusion of the first fluid along the first flow path to the infusion of the second fluid along the second path; further comprising transmitting a control signal to begin the infusion; further comprising transmitting a control signal to stop the infusion.

BRIEF DESCRIPTION OF THE DRAWINGS

FIGS. 4A-4O are schematic diagrams of a screen for an infusion pump system with common line auto flush in accordance with the present invention.

Like elements share like reference numbers throughout the various figures.

DETAILED DESCRIPTION OF THE PREFERRED EMBODIMENT

Systems and methods that improve an infusion pump system with common line are described herein. The infusion pump can deliver a first fluid from a first reservoir, then switch to delivering a second fluid from a second reservoir as per patient requirements. As discussed above, switching may result in some of the first fluid remaining in a common line. Furthermore, delivering fluids at rates other than the desired rates may result in air in the line or inaccurate therapy, which can be fatal to the patients. The systems and methods described here can improve delivery and accurately account for the first fluid remaining in the internal volume of the common line. Fluid as used herein can be any fluid suitable to be administered to a patient by infusion, including saline fluid, fluid including a drug or other therapeutic agent, or the like.

Figure 1A:
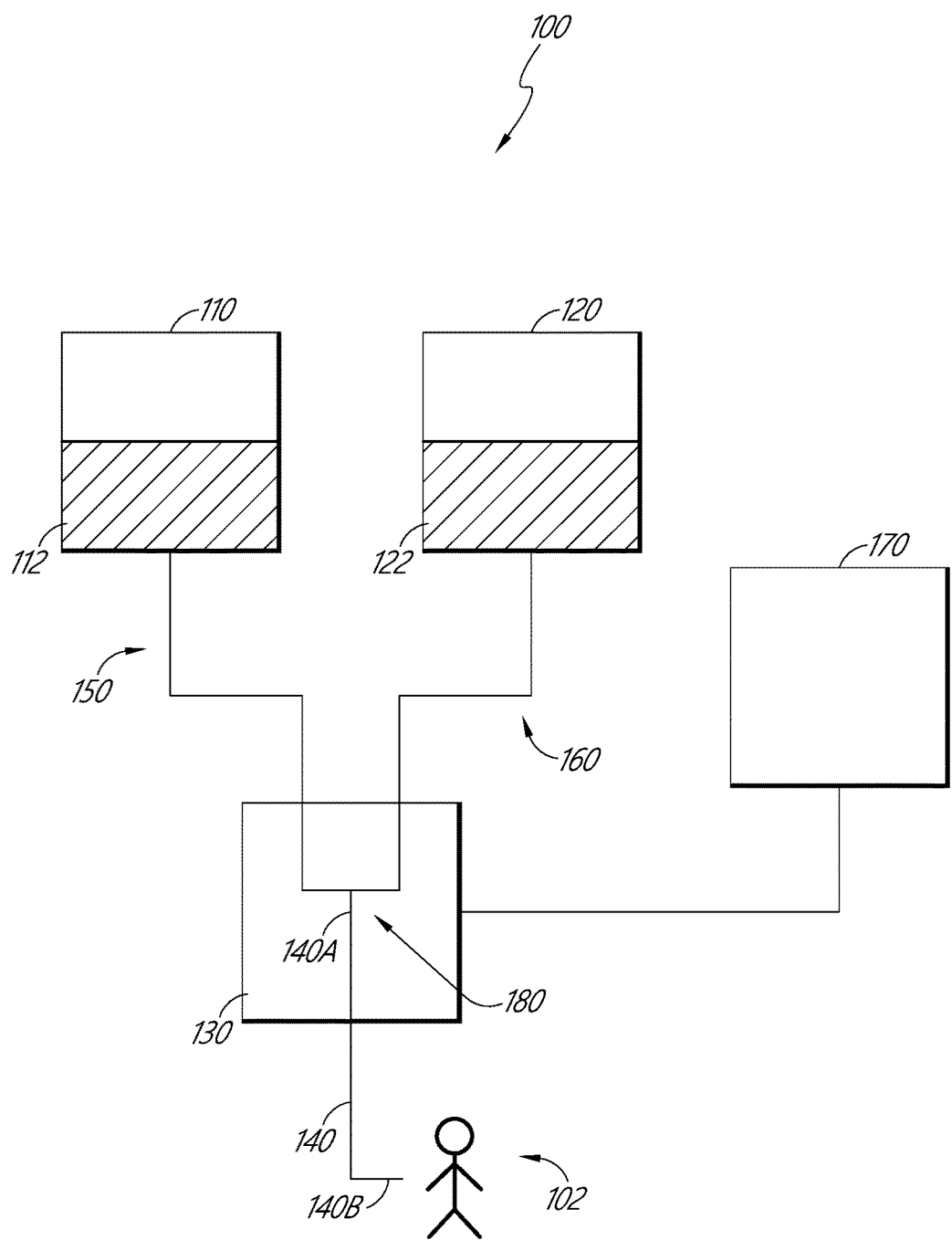
FIGS. 1A & 1B are block diagrams of infusion pump systems with common line auto flush in accordance with the present invention.
Figure 1B:
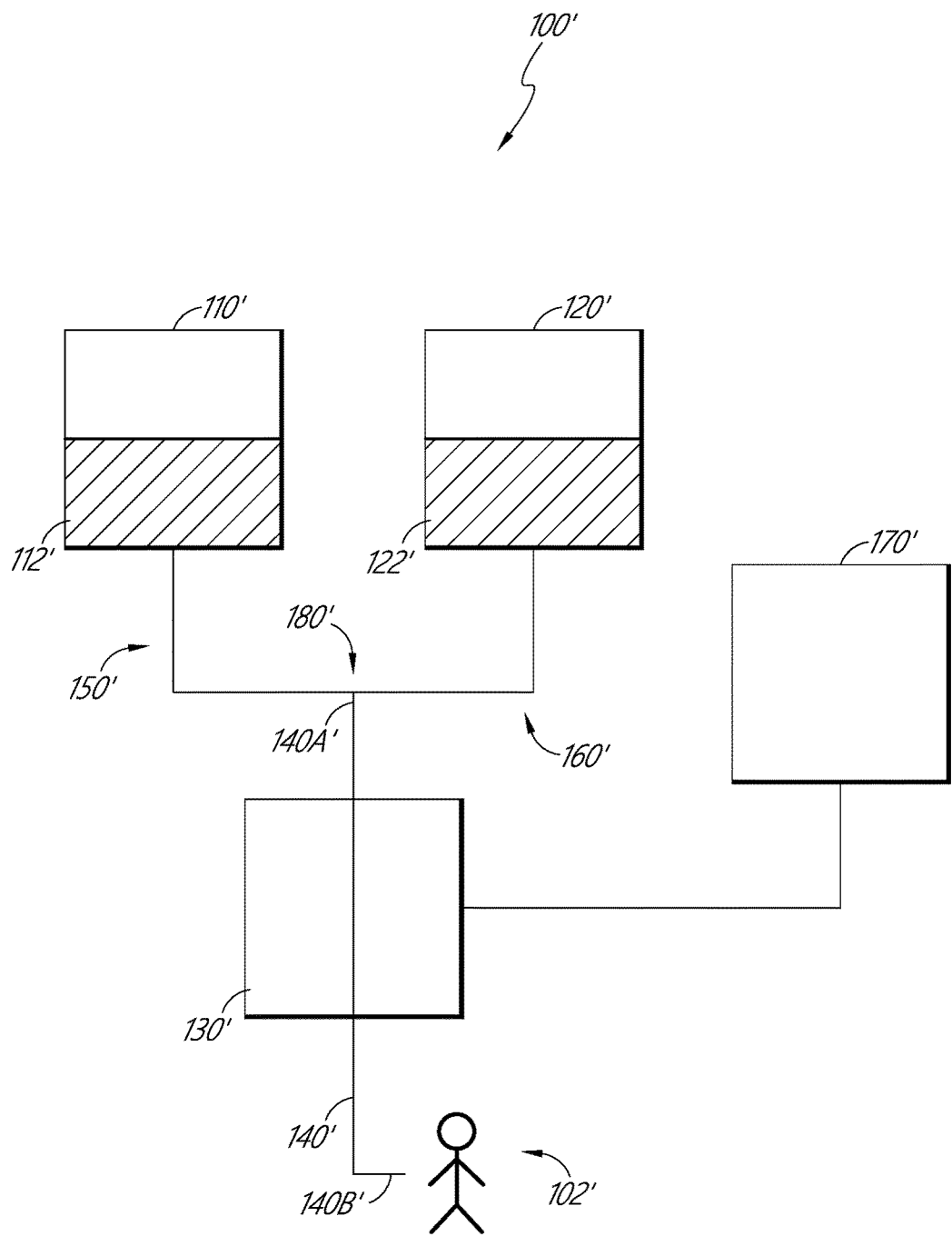

FIGS. 1A & 1B are block diagrams for embodiments of infusion pump systems with common line. The infusion pump system illustrated in FIG. 1A includes a junction in fluid communication with the first reservoir and the second reservoir internal to the infusion pump, while the embodiment of the infusion pump system illustrated in FIG. 1B has a junction in fluid communication with the first reservoir and the second reservoir external to the infusion pump. The location of the junction, in part, determines the length and internal volume of the common line between the junction and the terminal fluid delivery end. The internal shape, which is usually substantially circular, and the diameter of the common line are factors along with the length that determine the internal volume, although other shapes can be used without detracting from the scope of the disclosure.

The infusion pump system 100 of FIG. 1A includes a junction 180 internal to the infusion pump 130. The infusion pump system 100 includes a first reservoir 110 that can contain a first fluid 112; a second reservoir 120 that contain a second fluid 122; a junction 180 in fluid communication with the first reservoir 110 and the second reservoir 120; a common line 140 in fluid communication with the junction 180 at one end 140A and having a terminal fluid delivery end 140B for connection to the patient 102, and an infusion pump 130 operable to drive fluid through the common line 140. The infusion pump 130 is operable to: infuse the first fluid 112 at a first rate along a first flow path 150 including the first reservoir 110, the junction 180, and the common line 140; receive a common line flush volume value for the common line 140; switch from the first flow path 150 to a second flow path 160 including the second reservoir 120, the junction 180, and the common line 140; drive the second fluid 122 at the first rate along the second flow path 160; monitor volume of the second fluid 122 driven at the first rate; and drive the second fluid 122 at a second rate along the second flow path 160 when the monitored volume is equal to or greater than the common line flush volume value. In one example, the infusion pump 130 can be a fluid displacement pump employing a cassette, such as the Plum 360™ infusion pump available from Hospira, Inc. of Lake Forest, Ill. Those skilled in the art will appreciate that the infusion pump 130 can be any type of pump operable to drive fluid through the common line 140.

In one embodiment, the infusion pump 130 can be operably connected to a medication management unit (MMU) 170 to receive a drug library including the desired common flush volume value from the MMU 170. In one embodiment, the infusion pump 130 can be further operable to increment a first fluid displayed volume by the monitored volume when the second fluid 122 is driven at the first rate along the second flow path 160. The infusion pump 130 can be further operable to increment a second fluid displayed volume by the monitored volume when the monitored volume is equal to or greater than an internal volume of the common line. In one embodiment, the infusion pump 130 can be operable to stop infusing the first fluid 112 before driving the second fluid 122 at the first rate along the second flow path 160. In one embodiment, the infusion pump 130 can be operable to monitor the volume of the first fluid and switch to delivery of the flush volume when the volume of the first fluid is equal to the received Volume to be Infused (VTBI) for the first fluid. In another embodiment, the infusion pump 130 can be operable to monitor the first fluid path and switch to delivery of the flush volume when the infusion pump detects a given threshold of air (as a single bubble, accumulated bubbles, or by percentage volume) in the first fluid path.

The infusion pump 130 can be operable to receive the common line flush volume value for the common line 140 automatically from the drug library stored in a memory locally in the infusion pump system 100 or remotely on a server. In one example, the drug library associates the common flush volume value with a particular therapeutic agent. In another example, the drug library associates the common flush volume value with a particular clinical care area (CCA), such as general care, an intensive care unit (ICU), a neonatal ICU, or the like. In yet another example, the drug library associates the common flush volume value with a particular consumable infusion set, which directly provides the common line volume. The drug library can include upper and lower dosing limits with hard and soft limits for a number of therapeutic agents. In another embodiment, the infusion pump 130 can be operable to receive the common line flush volume value for the common line 140 from a caregiver via an input on a user interface of the infusion pump. In another embodiment, the infusion pump 130 can be operable to receive the second rate at which the second fluid is delivered when the monitor volume is equal to or greater than the common line flush volume value.

The common line 140 as illustrated includes the line between the junction 180 and the terminal fluid delivery end 140B that is generally connectable at the patient 102, and includes any fluid path common to the first flow path 150 and the second flow path 160. Thus, the common line 140 can include flow paths within the infusion pump 130 (including the associated consumable infusion set, when applicable) common to the first flow path 150 and the second flow path 160, and is not limited to tubing external to the infusion pump 130. The common line 140 is any portion of the infusion pump system 100 through which the first fluid 112 or the second fluid 122 can alternately flow when switched. In one embodiment, the common line flush volume value is an internal volume of the common line 140. Those skilled in the art will appreciate that the common line flush volume value can include an associated consumable infusion set volume, extension sets, filters, patient access devices, catheters, and the like, as required for a particular setup of the infusion pump system 100. In another embodiment, the common line flush volume value is an internal volume of the common line 140 plus an adjustment volume. The adjustment volume can be any volume desired as a safety factor to assure that the common line 140 is free of the first fluid 112 before the second fluid 122 is infused at the second rate.

The infusion pump system 100' of FIG. 1B has a junction 180' external to the infusion pump 130'. The infusion pump system 100' includes a first reservoir 110' containing a first fluid 112'; a second reservoir 120' containing a second fluid 122'; a junction 180' in fluid communication with the first reservoir 110' and the second reservoir 120'; a common line 140' in fluid communication between the junction 180' and the terminal fluid delivery end 140B' that is generally connectable at the patient 102', and an infusion pump 130' operable to drive fluid through the common line 140'. The infusion pump 130' is operable to: infuse the first fluid 112' at a first rate along a first flow path 150' including the first reservoir 110', the junction 180', and the common line 140'; receive a common line flush volume value for the common line 140'; switch from the first flow path 150' to a second flow path 160' including the second reservoir 120', the junction 180', and the common line 140'; drive the second fluid 122' at the first rate along the second flow path 160'; monitor volume of the second fluid 122' driven at the first rate; and drive the second fluid 122' at a second rate along the second flow path 160' when the monitored volume is equal to or greater than the common line flush volume value. In one embodiment, the junction 180' can include a two-way valve to manually or automatically switch the infusion pump system 100' between the first flow path 150' and the second flow path 160'. In one example, the infusion pump 130' can be a peristaltic pump, such as the pump used in the Sapphire™ infusion system available from Hospira, Inc. of Lake Forest, Ill. Those skilled in the art will appreciate that the infusion pump 130' can be any type of pump operable to drive fluid through the common line 140'.

Figure 2:
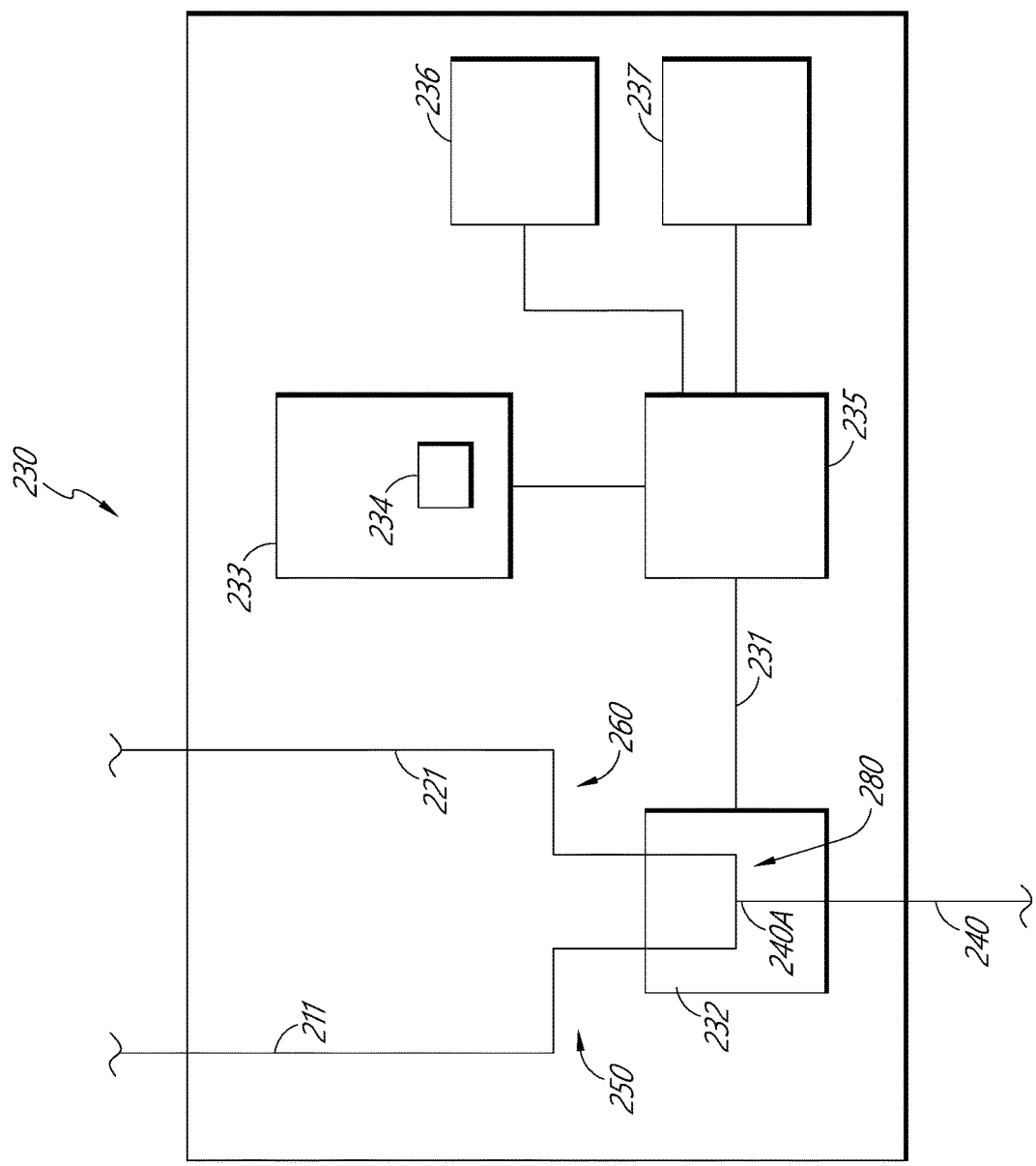
FIG. 2 is a block diagram of an infusion pump with common line auto flush in accordance with the present invention.

FIG. 2 is a block diagram of an embodiment of an infusion pump with common line auto flush. The infusion pump 230 is operably connected to a common line 240 in fluid communication with a junction 280 at one end 240A and having a terminal fluid delivery end 240B (not shown due to truncation), the junction 280 being in fluid communication with a first reservoir (not shown) containing a first fluid and a second reservoir (not shown) containing a second fluid. In this example, a first reservoir line 211 provides fluid communication between the first reservoir and the junction 280 and a second reservoir line 221 provides fluid communication between the second reservoir and the junction 280.

The infusion pump 230 includes a memory 233 operable to store programming code; a flow controller 235 operably connected to the memory 233; and a fluid driver 232 operably connected to receive a control signal 231 from the flow controller 235, the fluid driver 232 being operable to drive fluid through the common line 240. The flow controller 235 is operable to execute the programming code and provide the control signal 231 to the fluid driver 232 in response to the programming code. The fluid driver 232 is responsive to the control signal 231 to infuse the first fluid at a first rate along a first flow path 211 including the first reservoir, the junction 280, and the common line 240; receive a common line flush volume value for the common line 240; switch from the first flow path 250 to a second flow path 260 including the second reservoir, the junction 280, and the common line 240; drive the second fluid at the first rate along the second flow path 260; monitor volume of the second fluid driven at the first rate; and drive the second fluid at a second rate along the second flow path 260 when the monitored volume is equal to or greater than the common line flush volume value. In an embodiment, the flow controller 235 monitors the volume based on a time elapsed and a rate of delivery. The flow controller 235 can also monitor volume based on measurements, such as number of turns of a motor or signals from a sensor.

The flow controller 235 can be any hardware processor, microprocessor, or the like responsive to the programming code to generate the control signal 231. The fluid driver 232 can be any metered pump, such as a cartridge pump, syringe pump, peristaltic pump, or the like, operable to drive fluid at a desired rate in response to the control signal 231. In one embodiment, the fluid driver 232 can be further responsive to the control signal 231 to increment a first fluid displayed volume by the monitored volume when the second fluid is driven at the first rate along the second flow path 260. The fluid driver 232 can be further responsive to the control signal 231 to increment a second fluid displayed volume by the monitored volume when the monitored volume is equal to or greater than an internal volume of the common line 240. The first fluid displayed volume and/or the second fluid displayed volume can be displayed on a user interface 236. In another embodiment, the fluid driver 232 can be responsive to the control signal 231 to stop infusing the first fluid before driving the second fluid at the first rate along the second flow path 260.

The memory 233 can also be operable to store data, such as a drug library 234 including the common flush volume value, which can optionally be associated with a particular therapeutic agent, a particular clinical care area, and/or a particular consumable infusion set. Different therapeutic agents may have different fluid properties and thus it may be advantageous in some embodiments to associate particular common flush volume value with particular therapeutic agents. In one embodiment, the infusion pump 230 can receive the common line flush volume value for the common line 240 automatically from the drug library 234. In another embodiment, the infusion pump 230 can receive the common line flush volume value manually via direct entry of the value on a user interface 236. The manual entry can be accomplished using a manufacturer provided volume value based upon the length and internal diameter of the common line 240 or a list number or other identifier that is used to access an associated volume value from a lookup table in the pump memory 233, drug library or MMU. The possibility for manual typographical errors can be reduced by use of a barcode, radio frequency (RFID), optical, touch memory reader, near field communicator, or the like to input or scan a machine readable identifier on the infusion set, common line, or its package to obtain the volume value, the list number or other identifier associated with the volume value.

The infusion pump 230 can include human and/or machine interfaces as desired for a particular application. A user interface 236 operably connected to the flow controller 235 can provide input from and/or output to a caregiver or other user to the infusion pump 230. Exemplary user interfaces can include display screens, soft keys or fixed keys, touchscreen displays, and the like. An I/O interface 237 operably connected to the flow controller 235 can provide input from and/or output to hardware associated with the infusion pump 230. Exemplary I/O interfaces can include a wired and/or wireless interface to an electronic network, medication management unit (MMU), medication management system (MMS), or the like.

The common line flush volume value can be selected as desired for a particular application. The common line 240 includes the line between the junction 280 and the terminal fluid delivery end 240B, and includes any fluid path common to the first flow path 250 and the second flow path 260 and so can include any portion of the infusion pump 230 (including the associated consumable infusion set, when applicable) through which the first fluid or the second fluid can alternately flow. In one embodiment, the common line flush volume value is equal to the internal volume of the common line 240, so that the second fluid is infused at the second rate along the second flow path as soon as the first fluid has been cleared from the common line 240. In another embodiment, the common line flush volume value is equal to the internal volume of the common line 240 plus an adjustment volume (to take into account the added/subtracted volume of other connectors or components), so that the second fluid is infused at the second rate along the second flow path after the first fluid has been cleared from the common line 240 plus the adjustment volume of the second fluid has been delivered at the first rate. In another embodiment, the common line flush volume value is equal to the internal volume of the common line modified by a percentage, which could provide a desired overage or underage. The adjustment volume can be used as a safety factor to assure that the common line 240 is free of the first fluid before the second fluid is infused at the second rate.

Figure 3:
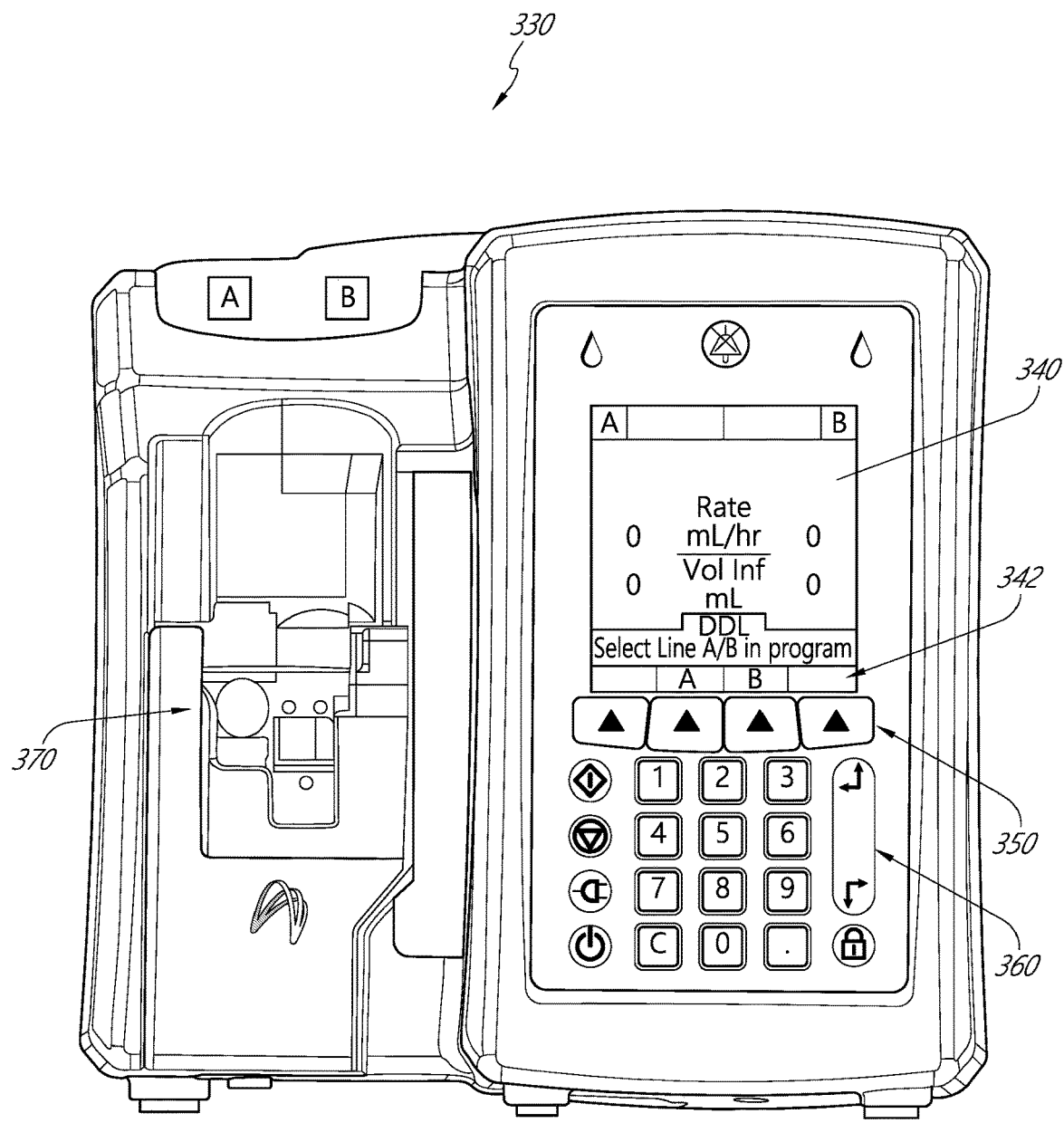
FIG. 3 is a schematic diagram of an infusion pump with common line auto flush in accordance with the present invention.

FIG. 3 is a schematic diagram of an infusion pump with common line auto flush in accordance with the present invention. In this example, the infusion pump 330 includes a display 340, soft keys 350, and fixed keys 360 as a user interface. The display 340 provides operational and/or programming information to the user. The soft keys 350 perform different functions depending on the command displayed on an adjacent command portion 342 of the display 340. The fixed keys 360 are labeled with an input or function which functions the same, regardless of whatever is displayed on the display 340. In this example, the infusion pump 330 also includes a pump mechanism 370 operable to communicate with the first reservoir line and the second reservoir line and to move the first fluid or the second fluid to the terminal fluid delivery end of the common line.

Figures 4C, 4D:
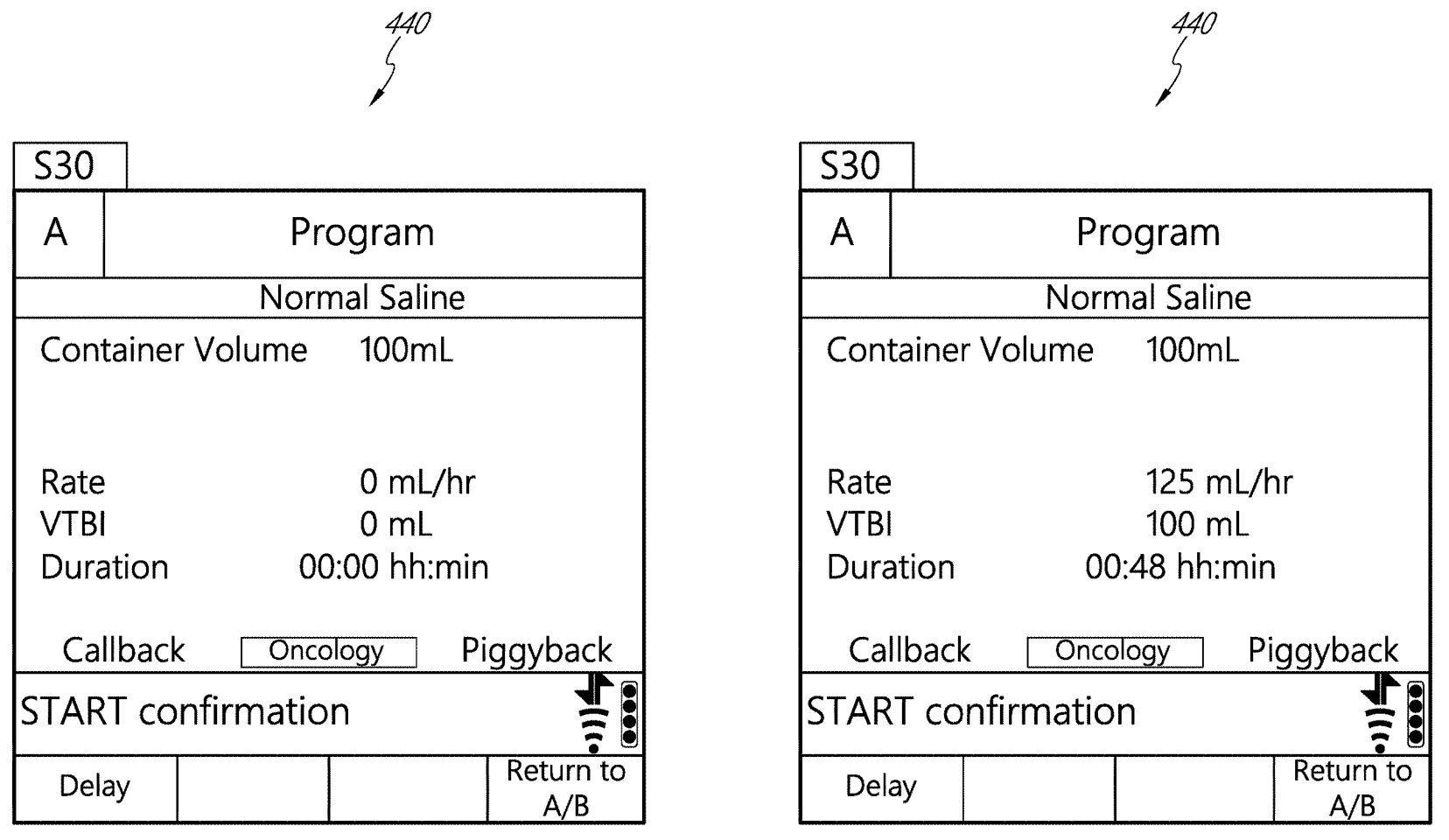
Figures 4E, 4F:
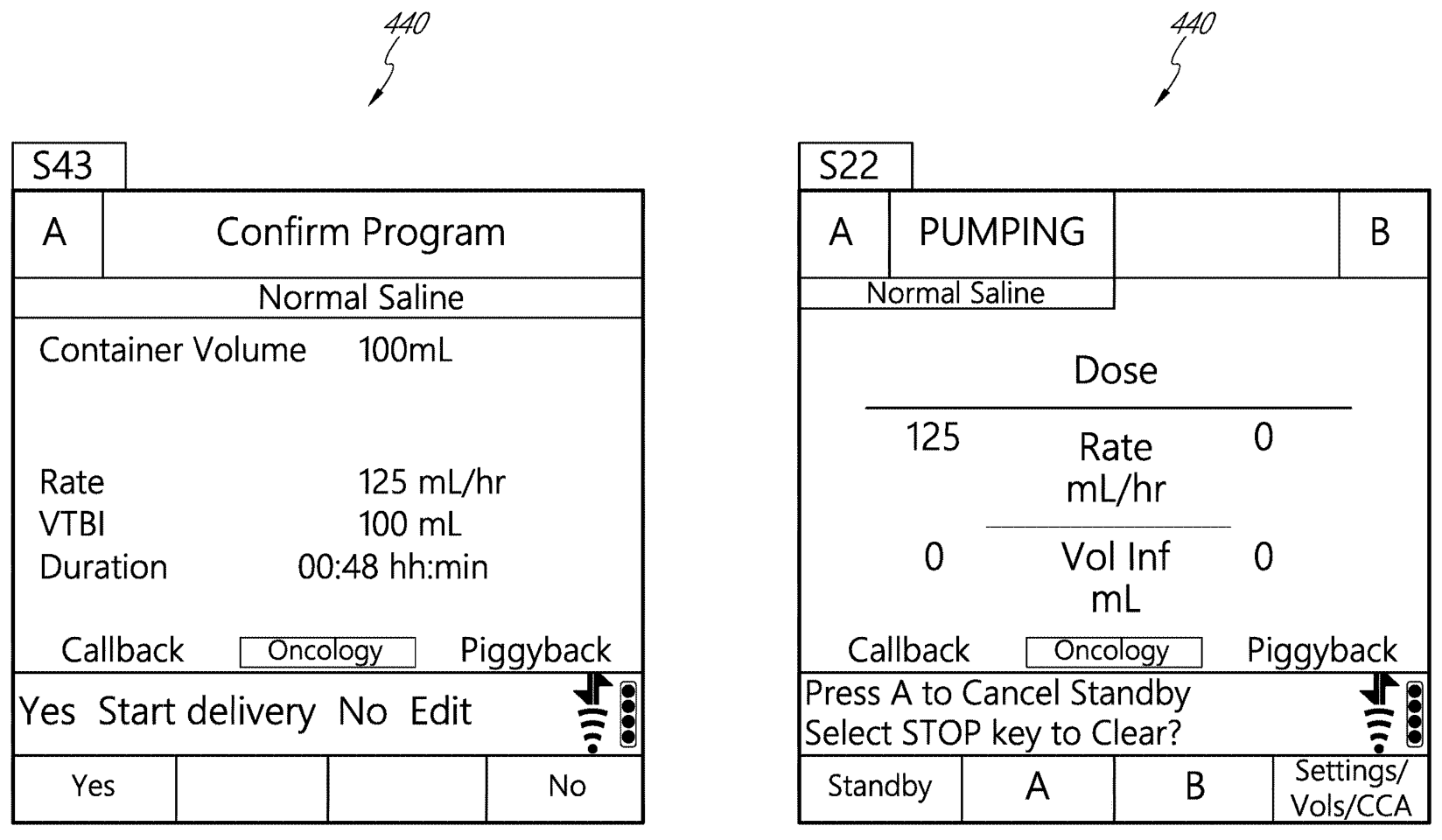
Figure 4O:

FIGS. 4A-4O illustrate schematic diagrams of user interfaces or screens for an infusion pump system with common line auto flush. In this embodiment, the user can manually edit the common line flush volume value, i.e., the flush volume. In this example, the infusion pump is infusing a first fluid to the terminal fluid delivery end of the common line on Channel A at a first rate, switches to infusing a second fluid to the terminal fluid delivery end of the common line on Channel B at a second rate, then switches back to infusing the first fluid on Channel A but maintains the second rate long enough to clear the remaining second fluid from the common line before changing to the first rate. The flow controller can control the switching using one or more control signals. In some embodiments, the reservoirs may be arranged to switch automatically based on fluid dynamics and arrangement of the reservoirs with respect to each other.

Referring to FIG. 4A, the screen 440 indicates that the infusion pump is in Standby, awaiting programming. The user actuates the soft key associated with Channel A at the bottom of the screen 440 to access a new screen to program Channel A parameters starting with FIG. 4B. Referring to FIG. 4B, the user highlights one of the drugs from a displayed drug list (in this example, Normal Saline) and actuates the soft key associated with Choose at the bottom of the screen 440 to access a new screen to program infusion parameters for the highlighted drug. Referring to FIG. 4C, the user enters values for the Rate, Volume to Be Infused (VTBI), and/or Duration parameters for the infusion of the selected drug (in this example, Normal Saline) for Channel A. Those skilled in the art will appreciate that the parameters can be interrelated, such that the infusion pump automatically fills in the values for some of the parameters once values for other parameters have been entered. Referring to FIG. 4D, the program infusion parameters entered for Channel A are displayed, with a Rate of 125 mL/hr, VTBI of 100 mL and Duration of 00:48 hh:mm. The user actuates the START fixed key to confirm the values entered and to access the Confirm Program screen of FIG. 4E. To start delivery on Channel A, the user actuates the soft key associated with Yes at the bottom of the screen 440 of FIG. 4E, which switches the screen 440 to FIG. 4F indicating that Channel A is infusing the Channel A drug (in this example, Normal Saline) at the Channel A Rate of 125 mL/hr with a Volume Infused of 0 mL.

Referring to FIG. 4F, the user actuates the soft key associated with Channel B at the bottom of the screen 440 to access a new screen to program Channel B parameters starting with FIG. 4G. In this embodiment, the pumping of the first fluid on Channel A continues until the pumping of the second fluid on Channel B is initiated. In another embodiment, the pumping of the first fluid on Channel A can be stopped before pumping the second fluid on Channel B, e.g., while the common line auto flush is being programmed.

Referring to FIG. 4G, the user highlights one of the drugs from a displayed drug list (in this example, NIVOlumab) and actuates the soft key associated with Choose at the bottom of the screen 440 to access a new screen 440 on FIG. 4H to program infusion parameters for the highlighted drug. The user enters values for the Dose, Rate, Volume to Be Infused (VTBI), and/or Duration parameters for the infusion of the selected drug (in this example, NIVOlumab) for Channel B. Those skilled in the art will appreciate that the parameters can be interrelated, such that the infusion pump automatically fills in the values for some of the parameters once values for other parameters have been entered. Referring to FIG. 4I, the program infusion parameters entered for Channel B are displayed, with a Dose of 100 mcg/kg/min, a Rate of 375 mL/hr, a VTBI of 500 mL, and a Duration of 1:20 hh:mm.

To proceed from the screen 440 of FIG. 4I to FIG. 4J to program the common line auto flush parameters, the user actuates the soft key associated with Flush Line (in this example, Auto Flush) at the bottom of the screen 440. In one embodiment, the Flush Line only appears at the bottom of the screen 440 when a first and second fluid are to be infused sequentially through a common line, i.e. for a piggyback infusion and another prior or subsequent infusion. Accordingly, in an embodiment, the flow controller 235 can detect a piggyback infusion and automatically generate a user interface as illustrated to provide an option to select flush parameters. The flow controller 235 may also automatically select flush parameters, such as the common line flush volume from the drug library based on the detection of instructions to switch infusion from the first fluid to the second fluid.

Referring to FIG. 4J, the user can enter the Flush Volume. In this example, the Flush Volume is limited to a maximum flush volume value, such as 30 mL. Those skilled in the art will appreciate that the maximum flush volume value can be selected as desired for a particular therapeutic agent, particular clinical care area, or the like and can be provided through a drug library as desired. Referring to FIG. 4K, the user has entered a value of 20 mL for the Flush Volume. The Rate remains at the previously entered Channel B Rate of 375 mL/hr as shown on FIG. 4I. In this example, the Rate is not editable and the Duration is calculated from the Rate and the Flush Volume. Referring to FIG. 4K, the user actuates the START fixed key to confirm the values entered and to access the Confirm Program screen of FIG. 4L, which shows the Channel B parameters.

In this embodiment, the Flush Volume can be edited by the user. In one example, the initial editable Flush Volume is displayed as a zero value as shown in FIG. 4J. In another example, the initial editable Flush Volume is displayed as a predetermined value, e.g., as a predetermined value provided through a drug library. In another embodiment, the Flush Volume is predetermined and cannot be edited by the user. The Flush Volume can be displayed as in FIG. 4K, but cannot be changed.

Referring to FIG. 4L, the user actuates the soft key associated with Yes at the bottom of the screen 440 to switch from the present Channel A infusion to the Channel B infusion. When the channel is switched, the Channel A drug (in this example, Normal Saline) remaining in the common volume is infused to the terminal fluid delivery end of the common line at the Channel B Rate of 375 mL/hr until the Channel A drug is cleared from the common volume and the Channel B drug (in this example, NIVOlumab) is infused at the Channel B Rate of 375 mL/hr. Referring to FIG. 4M, the Channel A infusion is on hold and Pending and Channel B is infusing the Channel B drug (in this example, NIVOlumab). In this example, the Volume Infused of Channel A drug (in this example, Normal Saline) of 3 mL was infused while the Channel B and flush volume parameters were being set.

Referring to FIG. 4N, Channel B has infused the desired VTBI of 500 mL so Channel B has stopped and Channel A has begun the common line auto flush, continuing the Channel B Rate of 375 mL/hr. When the infusion channel is switched (on reaching the desired Channel B VTBI), the Channel B drug (in this example, NIVOlumab) remaining in the common volume or common line is infused at the Channel B Rate of 375 mL/hr until the Channel B drug is cleared from the common volume or common line. Referring to FIG. 4O, Channel A has delivered the Flush Volume of 20 mL to the patient, clearing the Channel B drug remaining in the common volume or common line. The Channel A drug (in this example, Normal Saline) is then infused at the Channel A Rate of 125 mL/hr. The Volume Infused of Channel A drug (in this example, Normal Saline) has been increased by the Flush Volume of 20 mL (from 3 to 23 mL) to account for the Channel A drug remaining in the common volume or common line previously when switching from Channel A to Channel B.

In this example, the indicated Channel A Volume Infused is lower than the actual Channel A Volume Infused and the indicated Channel B Volume Infused is higher than the actual Channel A Volume Infused from the time of switching the infusion from Channel A to Channel B until the Flush Volume is added to the Channel A Volume Infused following the common line auto flush, the difference between indicated the and the actual being the Flush Volume. The difference is typically small relative to the indicated Volume infused, but those skilled in the art will appreciate that the indicated Volume Infused can be corrected as desired for a particular application.

Figure 5A:
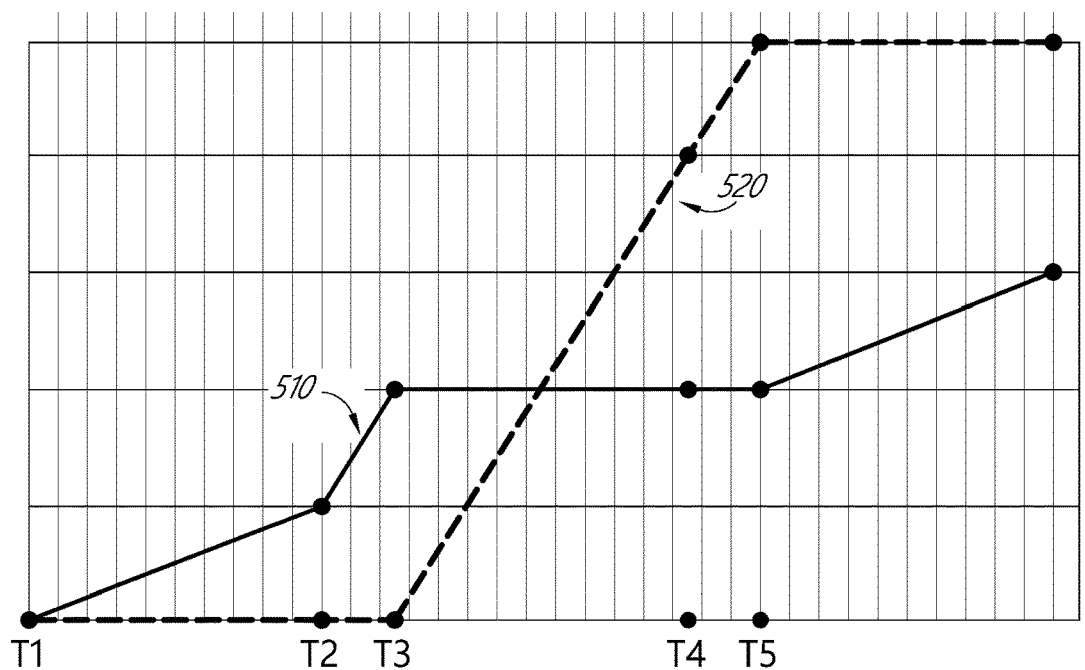
FIGS. 5A & 5B are graphs of fluid volume delivered at the terminal fluid delivery end of the common line versus time for a method of use for an infusion pump with common line auto flush in accordance with the present invention.
Figure 5B:
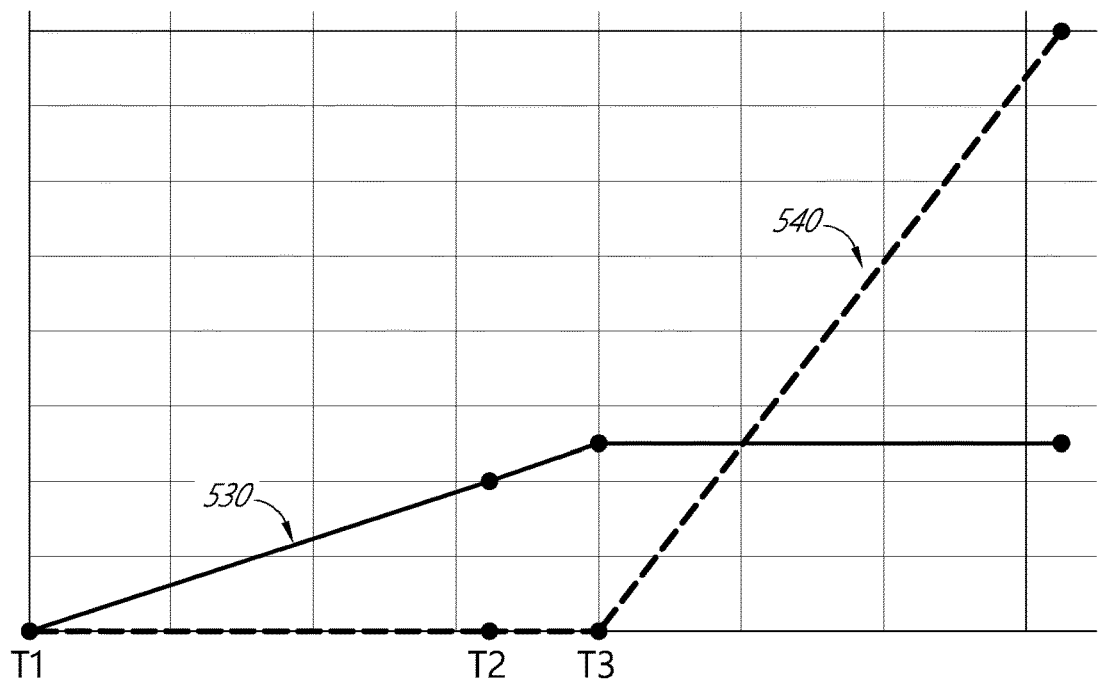

FIGS. 5A & 5B are graphs of fluid volume delivered at the terminal end of the common line or patient versus time for a method of use for an infusion pump with common line auto flush in accordance with the present invention. FIG. 5A illustrates the common line auto flush as described for FIGS. 4A-4O. FIG. 5B illustrates the common line auto flush as described for FIG. 6.

Referring to FIG. 5A, graph 510 is the fluid volume delivered at the terminal fluid delivery end of the common line for a first fluid versus time and graph 520 is the fluid volume delivered at the terminal fluid delivery end of the common line for a second fluid versus time. From T1 to T2, the first fluid is being infused at a first rate along a first flow path including the first reservoir and the second fluid is not being infused. From T2 to T3, the first fluid is being infused at a second rate along a second flow path including the second reservoir as the internal volume of the common line is cleared. The second fluid cannot be infused until the internal volume is cleared of the first fluid. From T3 to T4, the internal volume has been cleared of the first fluid so that no more first fluid is infused and the second fluid is infused at the second rate along the second flow path including the second reservoir. From T4 to T5, the auto flush is performed: the second fluid is infused at the second rate along the first flow path including the first reservoir as the internal volume of the common line is cleared. The first fluid cannot be infused until the internal volume is cleared of the second fluid. After T5, the first fluid is infused at the first rate along the first flow path including the first reservoir after the internal volume of the common line has been cleared of the second fluid. In this example, no additional second fluid is infused after T5.

Those skilled in the art will appreciate that the transition between the two fluids can be selected as desired for a particular application. In the example of FIG. 5A, a common line auto flush is performed from T4 to T5, but not from T2 to T3. As long as the common line flush volume value is known, the common line auto flush maintaining the first rate between T2 and T3 can be performed as desired.

Referring to FIG. 5B, graph 530 is the fluid volume delivered at the terminal fluid delivery end of the common line for a first fluid versus time and graph 540 is the fluid volume delivered at the terminal fluid delivery end of the common line for a second fluid versus time. From T1 to T2, the first fluid is infused at the first rate along a first flow path including the first reservoir and the second fluid is not being infused. From T2 to T3, the flow path is switched from the first flow path including the first reservoir to the second flow path including the second reservoir, and the second fluid is driven at a first rate along the second flow path to perform the common line auto flush. The first fluid is infused, driven or displaced until the internal volume of the common line has been cleared of the first fluid. After T3, the second fluid is infused, driven or displaced at the second rate along the second flow path including the second reservoir after the internal volume of the common line has been cleared of the first fluid. In one embodiment, the common line has been cleared of the second fluid when the monitored volume of the second fluid driven at the first rate between T2 and T3 is equal to or greater than the common line flush volume value. In this example, no additional second fluid is infused after T3.

Figure 6:
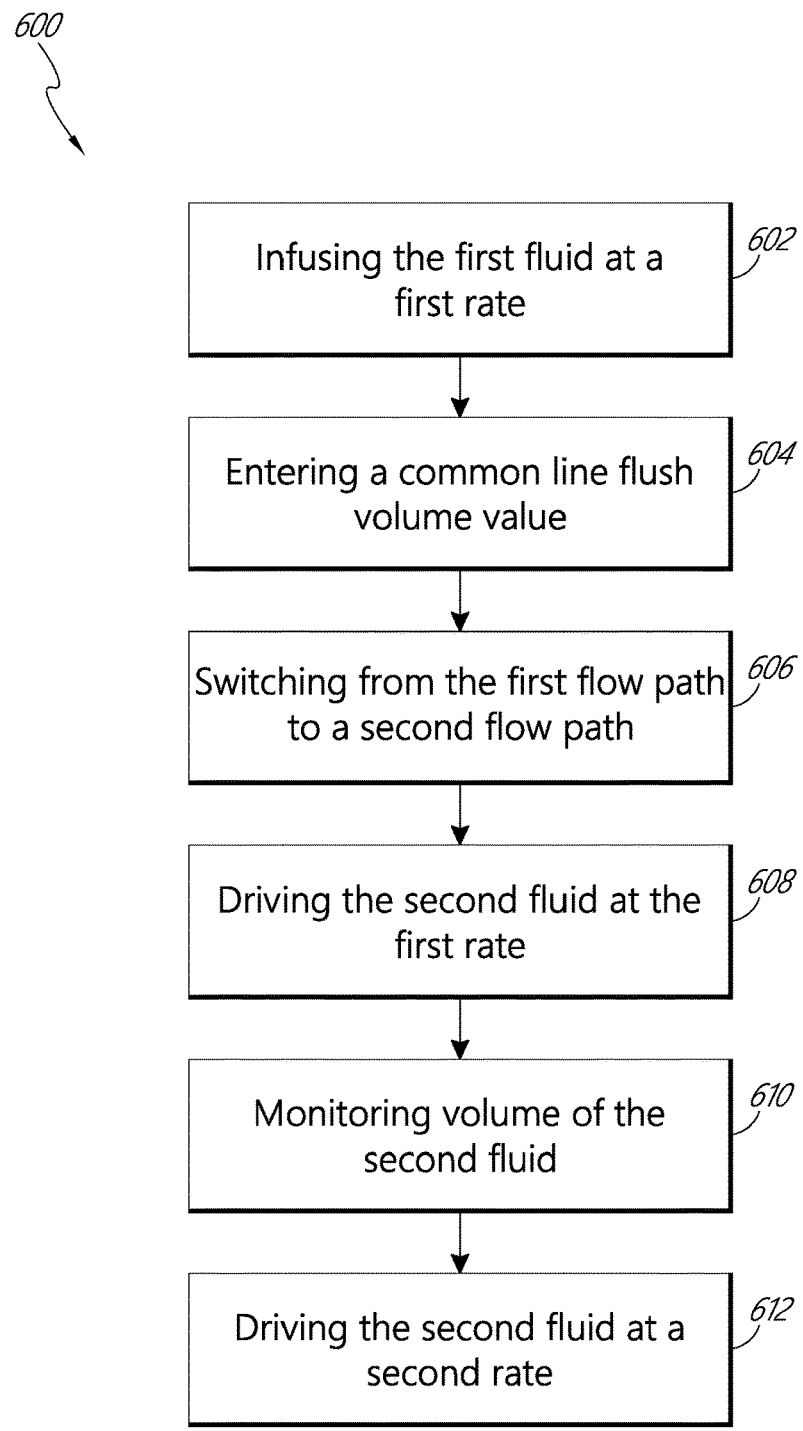
FIG. 6 is a flowchart of a method of use for an infusion pump system with common line auto flush in accordance with the present invention.

FIG. 6 is a flowchart of an embodiment of a method for common line auto flush. The method 600 to infuse with an infusion pump system can use an infusion pump system having a first reservoir containing a first fluid, a second reservoir containing a second fluid, a junction in fluid communication with the first reservoir and the second reservoir, a common line in fluid communication with the junction at one end and having a terminal fluid delivery end, and an infusion pump operable to drive fluid through the common line. The method 600 can be performed by any of the systems discussed above. In an embodiment, some or all aspects of the method 600 are stored as programmed instructions to be executed by the flow controller 235. The method 600 can be used with an infusion pump system and infusion pump as described in FIGS. 1A, 1B, & 2 above. In this example, the infusion pump is infusing a first fluid on a first flow path at a first rate and switches to infusing a second fluid on second flow path, maintaining the first rate long enough to clear the remaining first fluid from the common line before changing to a second rate for infusing the second fluid.

Referring to FIG. 6, at block 602, the infusion of the first fluid can be begin at a first rate along a first flow path including the first reservoir, the junction, and the common line. The infusion of the first fluid can be controlled by the flow controller 235 based on a control signal to activate the pump or other mechanical system. In some embodiments, the infusion of the first fluid can also be based on a user input or user control of the pump or the mechanical system. At block 604, the flow controller 235 can receive a common line flush volume value. As discussed above, the common line flush value can be received based on a user input via the user interfaces discussed above. In an embodiment, the flow controller 235 can automatically retrieve the common line flush volume value from the memory 233 or over a network. The common line flush volume may be predetermined for particular fluids. The common line flush volume may also depend on the VTBI or rate of the infusion.

At block 606, the flow controller 235 can determine to switch infusion from the first reservoir to the second reservoir. As discussed above, the infusion may also be switched based on the function of fluid dynamics and arrangement of the respective reservoirs without any determination from the flow controller 235. Switching changes the flow path from the first flow path to a second flow path, which includes the second reservoir, the junction, and the common line. In an embodiment, the flow controller 235 can control a valve to switch the flow path. At block 606, the second fluid is infused at the first rate 608 along the second flow path. The flow controller 235 can use control signals for the infusion of the second fluid and controlling the rate of delivery. By driving the second fluid at the first rate, the first fluid remaining in the common line is flushed and delivered to the patient at the same rate as therapeutically required. In some embodiments, the flow controller 235 obviates the need to specifically arrange the reservoirs by caregivers as the flow controller 235 can control the delivery instead of relying on fluid dynamics and gravity.

At block 610, the flow controller 235 can monitor volume of the second fluid 610 driven at the first rate. The flow controller 235 can determine that the monitored volume is equal to the common line flush volume value. When it's determined that common line flush volume value has been delivered, the flow controller 235 can begin infusion of the second fluid at a second rate along the second flow path as shown in block 612. In some embodiments, the flow controller 235 can track an amount of time before changing the rate of the second fluid delivery to the second rate. In one embodiment, the flow controller 235 can further include incrementing a second fluid displayed volume by the monitored volume when the monitored volume is equal to or greater than an internal volume of the common line. The flow controller 235 can thus accurately track the rate, time, and an amount of fluid delivered to the patient. In some embodiments, the flow controller 235 executes only some of the steps described above with respect to FIG. 6. Furthermore, the flow controller 235 can change the order of the steps, include additional steps, or modify some of the steps discussed above.

The common line flush volume value can be selected as desired for a particular application. In one embodiment, the common line flush volume value is an internal volume of the common line. In another embodiment, the common line flush volume value is an internal volume of the common line plus or minus an adjustment volume. The adjustment volume can be any volume desired as a safety factor to assure that the common line is free of the first fluid before the second fluid is infused at the second rate.

In one embodiment, the method 600 further includes incrementing a first fluid displayed volume by the monitored volume during the infusing the second fluid at the first rate along a second flow path, which can further include incrementing a second fluid displayed volume by the monitored volume when the monitored volume is equal to or greater than an internal volume of the common line.

Entering a common line flush volume value 604 for the common line can be performed manually or automatically. In one embodiment, the entering 604 includes manually entering the common line flush volume value on a user interface of the infusion pump. In another embodiment, the entering 604 includes automatically entering the desired common flush volume value from a drug library. The drug library can associate the desired common flush volume value with a particular therapeutic agent, a particular clinical care area, and/or a particular consumable infusion set.

In one embodiment, the switching from the first flow path to a second flow path 606 including the second reservoir, the junction, and the common line further includes stopping the infusing the first fluid before the driving the second fluid at the first rate along the second flow path.

FIGS. 7A-7E are schematic diagrams of use for an infusion pump system with common line auto flush in accordance with the present invention. FIGS. 7A-7E illustrate switching from infusing a first fluid to infusing a second fluid, then switching back to infusing the first fluid, while accounting for the previously infused fluid in the common line. In this example, the infusion pump is infusing a first fluid on a first flow path at a first rate and switches to infusing a second fluid on a second flow path, maintaining the first rate long enough to clear the remaining first fluid from the common line before changing to a second rate for infusing the second fluid. The infusion pump then switches to infusing a first fluid on the first flow path, maintaining the second rate long enough to clear the remaining second fluid from the common line before changing to a first rate for infusing the first fluid.

Figure 7C:
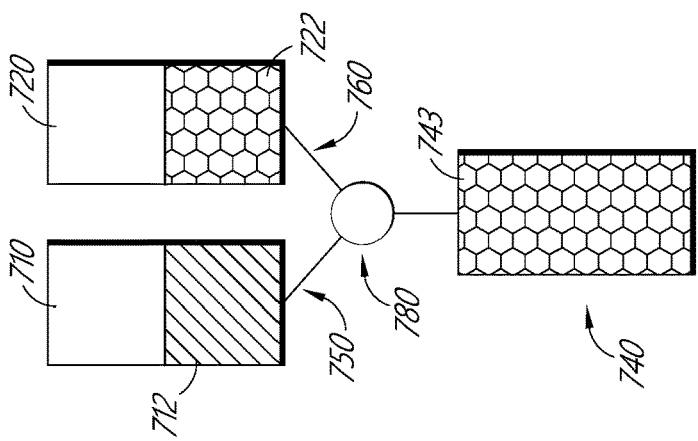
FIGS. 7A-7E are schematic diagrams of use for an infusion pump system with common line auto flush in accordance with the present invention.
Figure 7B:
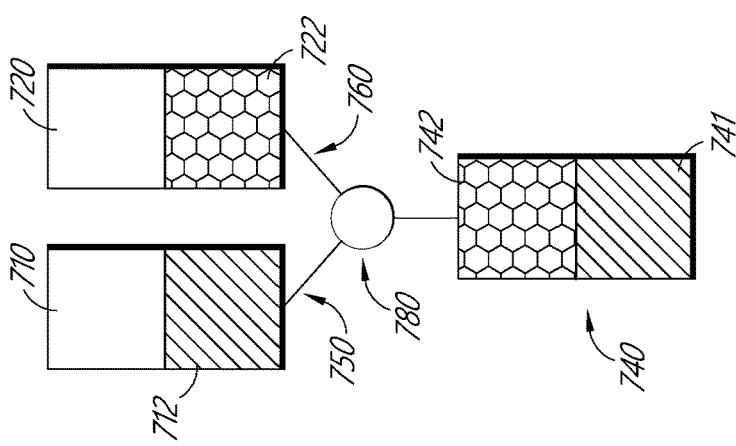
Figure 7A:
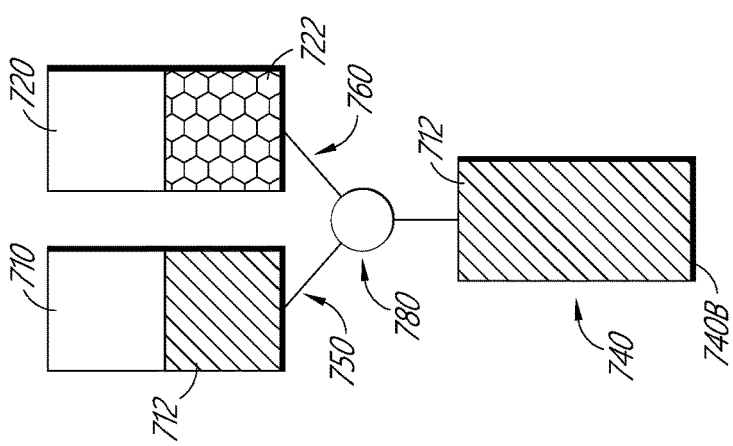

Referring to FIG. 7A, the first fluid 712 is being delivered to the terminal end 740B at a first rate along a first flow path 750 including the first reservoir 710, the junction 780, and the common line 740. The first fluid 712 is indicated by the diagonal lines. Referring to FIG. 7B, flow has been switched from the first flow path 750 to the second flow path 760 including the second reservoir 720, the junction 780, and the common line 740. The common line 740 contains first common line fluid 741 remaining from the initial infusion and indicated by the diagonal lines, and second common line fluid 742 indicated by the circles. The flow rate remains at the first rate because the remaining first common line fluid 741 is being delivered to the terminal fluid delivery end 740B or to the patient when connected. Referring to FIG. 7C, none of the first fluid remains in the common line 740, so the second common line fluid 743 is driven at a second rate along the second flow path 760.

Figure 7E:
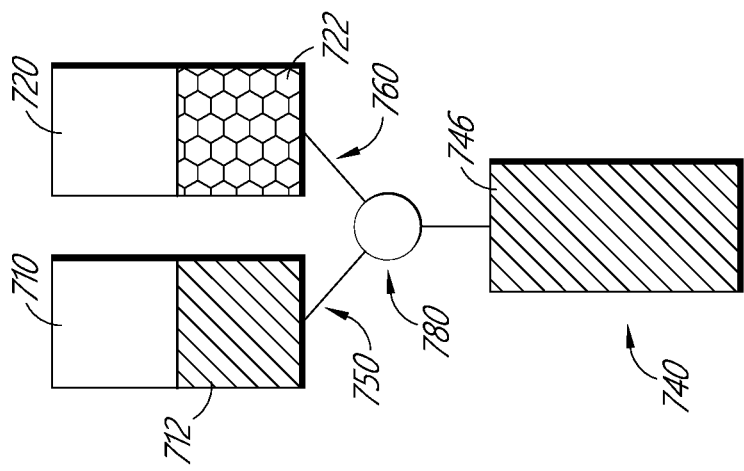
Figure 7D:
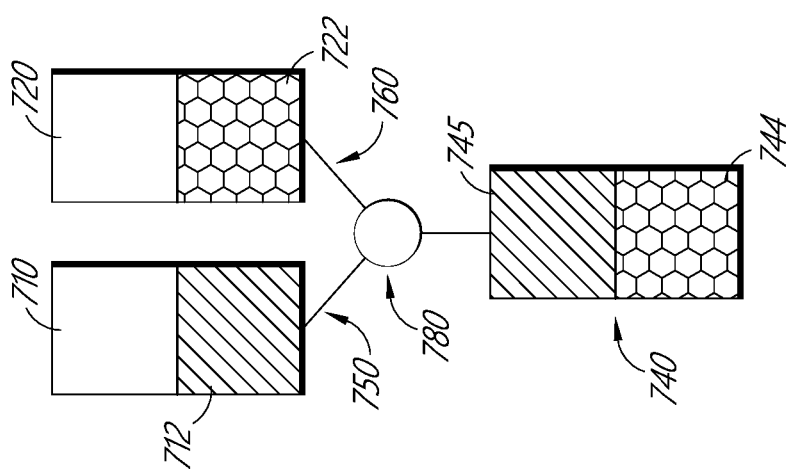

The use of the infusion pump system can also include switching back to infusing the first fluid. Referring to FIG. 7D, flow has been switched from the second flow path 760 to the first flow path 750. The common line 740 contains second common line fluid 744 remaining from the previous infusion indicated by the circles, and first common line fluid 745 indicated by the diagonal lines. The flow rate remains at the second rate because the remaining second common line fluid 744 is being delivered. Referring to FIG. 7E, none of the second fluid remains in the common line 740, so the first common line fluid 746 is driven at a first rate along the first flow path 750.

While the embodiments of the invention disclosed herein are presently considered to be preferred, various changes, rearrangement of steps, and modifications can be made without departing from the scope of the invention. The scope of the invention is indicated in the appended claims, and all changes that come within the meaning and range of equivalents are intended to be embraced therein.

What is claimed is:

1. A control system for controlling operation of an infusion pump system, the infusion pump system comprising a first reservoir configured to hold a first fluid, a second reservoir configured to hold a second fluid, a junction in fluid communication with the first reservoir and the second reservoir, a common line in fluid communication with the junction and having a terminal fluid delivery end, and an infusion pump operable to drive fluid through the common line toward the terminal fluid delivery end, the control system comprising one or more hardware processors configured to:

receive instructions for delivery of a first fluid at a first rate followed by a second fluid at a second rate;

infuse a first fluid at a first rate along a first flow path;

determine a first volume to clear the first fluid from a common line from a drug library, wherein the first volume is retrieved over a network and is associated with the first fluid;

infuse a second fluid at the first rate along a second flow path;

monitor a second volume of the second fluid infused at the first rate;

determine when the monitored volume of the second fluid meets or exceeds the first volume;

change infusion of the second fluid to a second rate along the second flow path based on the determination when the monitored volume of the second fluid meets or exceeds the first volume; and automatically generate a user interface configured to receive an input for the first volume only when sequential infusion is detected by a flow controller, said user interface further including a maximum flush volume corresponding to a particular therapeutic agent as retrieved over a network.

2. The control system of claim 1, wherein the first volume is received from a user input.

3. The control system of claim 1, wherein the first volume is stored in a memory.

4. The control system of claim 1, wherein the first volume is retrieved over a network.

5. The control system of claim 1, wherein the first volume is predetermined.

6. The control system of claim 1, wherein the first volume is based on the first fluid.

7. The control system of claim 1, wherein the first rate is different than the second rate.

8. The control system of claim 1, wherein the instructions for the delivery are received from an input via a user interface.

9. The control system of claim 1, wherein the one or more hardware processors are further configured to control a valve, wherein the valve is configured to switch the infusion of the first fluid along the first flow path to the infusion of the second fluid along the second path.

10. The control system of claim 1, wherein the one or more hardware processors are configured to transmit a control signal to begin the infusion.

11. The control system of claim 10, wherein the one or more hardware processors are configured to transmit a control signal to stop the infusion.

12. A method for controlling operation of an infusion pump system, the infusion pump system comprising a first reservoir configured to hold a first fluid, a second reservoir configured to hold a second fluid, a junction in fluid communication with the first reservoir and the second reservoir, a common line in fluid communication with the junction and having a terminal fluid delivery end, and an infusion pump operable to drive fluid through the common line toward the terminal fluid delivery end, the method comprising:

receiving instructions for delivery of a first fluid at a first rate followed by a second fluid at a second rate;

infusing a first fluid at a first rate along a first flow path;

determining a first volume to clear the first fluid from a common line from a drug library, wherein the first volume is retrieved over a network and is associated with the first fluid;

infusing a second fluid at the first rate along a second flow path;

monitoring a second volume of the second fluid infused at the first rate;

determining when the monitored volume of the second fluid meets or exceeds the first volume;

changing infusion of the second fluid to a second rate along the second flow path based on the determination when the monitored volume of the second fluid meets or exceeds the first volume; and automatically generating a user interface configured to receive an input for the first volume only when sequential infusion is detected by a flow controller, said user interface further including a maximum flush volume corresponding to a particular therapeutic agent as retrieved over a network.

13. The method of claim 12, wherein the first volume is received from a user input.

14. The method of claim 12, wherein the first volume is stored in a memory.

15. The method of claim 12, wherein the first volume is retrieved over a network.

16. The method of claim 12, wherein the first volume is retrieved over a network.

17. The method of claim 12, wherein the first volume is based on the first fluid.

18. The method of claim 12, wherein the first rate is different than the second rate.

19. The method of claim 12, wherein the instructions for the delivery are received from an input via a user interface.

* * * * *